United States Patent [19]
Hoppe et al.

[11] Patent Number: 5,912,272
[45] Date of Patent: *Jun. 15, 1999

[54] ACTIVE SUBSTANCES AND COMPOSITIONS FOR THE THERAPY OF SENILE XEROSIS

[75] Inventors: Udo Hoppe, Hamburg; Gerhard Sauermann, Wiemersdorf; Volker Schreiner; Klaus-Michael Steiger, both of Hamburg, all of Germany

[73] Assignee: Beiersdorf AG, Hamburg, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/718,591
[22] PCT Filed: Mar. 24, 1995
[86] PCT No.: PCT/EP95/01118
§ 371 Date: Dec. 23, 1996
§ 102(e) Date: Dec. 23, 1996
[87] PCT Pub. No.: WO95/26182
PCT Pub. Date: Oct. 5, 1995

[30] Foreign Application Priority Data

Mar. 25, 1994 [DE] Germany .............................. 44 10 238

[51] Int. Cl.$^6$ ...................................................... A61K 31/12
[52] U.S. Cl. ................................................................ 514/678
[58] Field of Search ................................................ 514/678

[56] References Cited

U.S. PATENT DOCUMENTS 5,378,461  1/1995  Neigut ..................................... 424/94.1

FOREIGN PATENT DOCUMENTS 0 461 333  12/1991  European Pat. Off. .
88/03015   5/1988   WIPO .

OTHER PUBLICATIONS

Patent Abstracts of Japan, vol. 8, No. 11(C–205), 1984.

*Primary Examiner*—Raymond Henley, III
*Attorney, Agent, or Firm*—Sprung Kramer Schaefer & Briscoe

[57] ABSTRACT

Use of topical formulations having a content of one or more compounds from the group consisting of ubiquinones and derivatives thereof for treatment of senile xerosis and/or exogenous ageing of the skin.

5 Claims, No Drawings

ACTIVE SUBSTANCES AND COMPOSITIONS FOR THE THERAPY OF SENILE XEROSIS

This application is a 371 of PCT/EP95/01118 filed Mar. 24, 1995.

DESCRIPTION

The present invention relates particularly to active compounds and formulations for treatment of senile xerosis.

Senile xerosis is caused, for example, by endogenous, genetically determined factors. In the epidermis and dermis, for example, the following age-related structural damage and dysfunctions which fall under the term "senile xerosis" occur:

a) Dryness, cracking, roughness and development of dryness wrinkles, itching (pruritus) and/or reduced re-oiling by sebaceous glands (for example after washing).

Exogenous factors, such as UV light and chemical noxae, can have a cumulative effect and, for example, accelerate or supplement the endogenous ageing processes. In the epidermis and dermis, for example, the following structural damage and dysfunctions which go beyond the extent and quality of the damage during chronological ageing and senile xerosis occur, in particular, in the skin due to exogenous factors:

b) visible dilation of vessels (couperosis);

c) flaccidity and development of wrinkles;

d) local hyper- and hypopigmentations and faulty pigmentations (for example senile keratosis) and e) increased susceptibility to mechanical stress (for example cracking).

The present invention particularly relates to active compounds and products for treatment of the secondary damage of skin ageing and senile xerosis, in particular the phenomena listed under a) to e).

Products for the care of aged skin are known per se. They comprise, for example, retinoids (vitamin A acid and/or derivatives thereof) or vitamin A and/or derivatives thereof. However, the extent of their action on the structural damage is limited. Furthermore, in product development, there are considerable difficulties in stabilizing the active compounds adequately against oxidative decay. The use of products comprising vitamin A acid moreover often causes severe erythematous skin irritations. Retinoids can therefore be employed only in low concentrations.

Cosmetic formulations with coenzyme Q-10 which are suitable for treatment of skin diseases, for prophylaxis of dystrophic and dysmetabolic states of the skin and for use in cases of chemical and physical respiratory damage or delayed respiration associated with age and wear are furthermore known from DE-A-33 09 850.

Japanese Laid-Open Specification 58,180,410 describes the suitability of coenzyme Q-10 for cosmetics. It is said to activate skin cell metabolism and suppress oxidation. As a result, coenzyme Q-10 has an important function in the prevention of skin damage due to UV rays and the prevention of ageing of the skin. In 20- to 40-year olds, the roughness of the skin is improved by the skin being given moisture.

The object of the present invention was thus to discover ways of avoiding the disadvantages of the prior art. In particular, the effect of eliminating the damage associated with senile xerosis and exogenous ageing of the skin is to be permanent, lasting and without the risk of side effects.

These objects are achieved by the invention.

The invention relates to the use of topical formulations having a content of one or more compounds from the group consisting of ubiquinones and derivatives thereof for treatment of senile xerosis and/or exogenous ageing of the skin.

The topical formulations according to the invention can be cosmetic or dermatological formulations.

The invention also relates to the use of one or more compounds from the group consisting of ubiquinones and derivatives thereof for treatment of senile xerosis and/or exogenous ageing of the skin.

It has been found, surprisingly, that ubiquinones and derivatives thereof not only protect the skin from damage due to chronological ageing of the skin, in particular ageing due to light, but also bring about the repair of damage already caused to the skin by senile xerosis and exogenous ageing of the skin, which significantly remedies the disadvantages of the prior art. The action of this group of substances on structural changes in senile skin is particularly advantageous.

"Ubiquinones" here also means "ubiquinones and derivatives thereof".

During senile xerosis, in particular, the following age-related structural damage and dysfunctions occur:

a) Dryness, roughness and development of small wrinkles, itching, reduced re-oiling by sebaceous glands (for example after washing).

During exogenous ageing of the skin, which is caused, for example, by UV light and chemical noxae, the following dysfunctions occur in particular:

b) visible dilation of vessels (couperosis);

c) flaccidity of the skin and development of wrinkles;

d) local hyper- and hypopigmentations and defective pigmentations (for example senile keratosis) and e) increased susceptibility to mechanical stress (for example cracking).

Ubiquinones are known from the literature (for example "Römpp Chemie Lexikon" [Römpp's Chemical Dictionary], Georg Thieme Verlag Stuttgart, New York, 9th Edition, pages 4784–4785 or "The Merck Index", 11th Edition, Merck & Co., Inc. Rahway, N.Y., USA, Abstr. 9751 (1989). They are also called mitoquinones or coenzyme Q. The number of isoprene units in the side chain is given by n in the designation coenzyme Q-n, wherein n is an integer. Preferred ubiquinones or coenzymes Q-n are those where n=0–12, particularly preferably n=1–12, and in particular n=6 to 10. The invention thus also relates to the quinone parent substance of ubiquinone without isoprene substituents. Ubiquinones according to the invention or derivatives thereof are, for example, also alkyl-ubiquinones, in particular 6-alkyl-ubiquinones, with preferably $C_1$–$C_{12}$-alkyl radicals. Decyl-ubiquinone, in particular 6-decyl-ubiquinone, or 2,3-dimethoxy-5-methyl-6-decyl-1,4-benzoquinone, is preferred.

During biological, mitochondrial oxidation, ubiquinones function as electron transfer agents and thus play a significant role in the energy metabolism of animal cells. Ubiquinones have been used for a long time in cosmetic formulations as antioxidants for protection of oxidation-sensitive substances.

The following active compounds according to the invention and combinations with these are particularly preferred:

coenzyme Q-10, coenzyme Q-9, coenzyme Q-8, coenzyme Q-7 and coenzyme Q-6.

The active compounds according to the invention can be present in the topical formulations in amounts of 0.001 to 99% by weight, for example also in amounts of 0.001 to 50% by weight, in each case based on the total weight of the formulations.

The active compounds according to the invention can preferably be present in the topical formulations in amounts of 0.01 to 10% by weight, in particular in amounts of 0.1 to 1% by weight, in each case based on the total weight of the formulations.

The skin care products or dermatological compositions especially preferably comprise 0.2 to 0.4% by weight, in particular 0.3% by weight, of coenzyme Q-10.

In the context of the Application, percentages by weight based on 100% of the total composition of the particular skin care preparation or dermatological composition according to the invention are always intended.

Topical formulations or compositions according to the invention with the combinations and active compounds according to the invention are all the customary use forms, for example creams (W/O, O/W, W/O/W), gels, lotions and milks.

The topical formulations according to the invention can be formulated as liquid, pasty or solid formulations, for example as aqueous or alcoholic solutions, aqueous suspensions, emulsions, ointments, creams, oils, powders or sticks. Depending on the desired formulation, the active compounds can be incorporated into pharmaceutical and cosmetic bases for topical applications, which can comprise, as further components, for example, oil components, fats and waxes, emulsifiers, anionic, cationic, ampholytic, zwitter-ionic and/or nonionic surfactants, lower mono- and polyhydric alcohols, water, preservatives, buffer substances, thickeners, fragrances, dyestuffs and opacifying agents. The active compounds according to the invention can advantageously also be used in transdermal therapeutic systems, in particular in cubic systems.

It is furthermore of advantage to add to the formulations antioxidants (for example alpha-tocopherol, vitamin E and C, imidazoles, alpha-hydroxycarboxylic acids (for example malic acid, glycolic acid, gluconic acid, salicylic acid and derivatives thereof) and/or iron complexing agents (for example EDTA and alpha-hydroxy-fatty acids) and/or known UV light protection filters, in amounts of, for example, 0.1 to 10 per cent by weight, in order to ensure the stability of the oxidation-sensitive ubiquinones or plastoquinones.

It is also advantageous to add to the formulations, in particular, 0.01–10 per cent by weight of substances or substance combinations of aerobic cell energy metabolism (for example cell energy transfer agents (such as creatine, guanine, guanosine, adenine, adenosine, nicotine, nicotinamide and riboflavin), coenzymes (for example pantothenic acid, panthenol, liponic acid and niacin), auxiliary factors (for example L-carnitine and uridine), substrates (for example hexoses, pentoses and fatty acids) and intermediate metabolism products (for example citric acid and pyruvate) and/or glutathione.

Formulations according to the invention can also advantageously comprise substances which absorb UV radiation in the UVA and/or UVB range, the total amount of the filter substances being, for example, 0.1% by weight to 30% by weight, preferably 0.5 to 10% by weight, in particular 1.0 to 6.0% by weight, based on the total weight of the formulations, in order to provide cosmetic formulations which protect the skin from the entire range of ultraviolet radiation. They can also be used as sunscreen compositions for the skin. In the formulations, the UV absorbers act as antioxidants with respect to the active compounds.

If the emulsions according to the invention comprise UVB filter substances, these can be oil-soluble or water-soluble. Oil-soluble UVB filters which are advantageous according to the invention are, for example: 3-benzylidenecamphor derivatives, preferably 3- (4-methylbenzylidene)camphor and 3-benzylidenecamphor.

Advantageous water-soluble UVB filters are, for example:

salts of 2-phenylbenzimidazole-5-sulphonic acid, such as its sodium, potassium or its triethanolammonium salt, and the sulphonic acid itself.

It can furthermore also be of advantage to combine active compound combinations according to the invention with UVA filters which have usually been contained to date in cosmetic formulations. These substances are preferably derivatives of dibenzoyl-methane, in particular 1-(4'-tert-butylphenyl)-3-(4'-methoxyphenyl)propane-1,3-dione and 1-phenyl-3-(4'-isopropylphenyl)propane-1,3-dione. The invention also relates to these combinations or formulations which comprise these combinations. The amounts used for the UVB combination can be employed.

The invention thus also relates to the combinations of the active compounds according to the invention, in particular in the topical formulations, with antioxidants, substances of aerobic cell energy metabolism and/or UV absorbers, with which, for example, the stability and the action of the formulation can be improved.

The examples given above for active compounds which can be combined from the active compound groups mentioned serve to describe the invention, without the intention being to limit the invention to these examples.

Protective formulation forms can furthermore be used, the substances according to the invention being included (encapsulated), for example, in liposomes, micelles, nanospheres and the like of, for example, hydrogenated amphiphiles, such as, for example, ceramides, fatty acids, sphingomyelin and phosphoglycerides, or in cyclodextrans. Further protection can be achieved by the use of a protective gas (for example $N_2$ or $CO_2$) during formulation and the use of gas-tight packaging forms.

Further auxiliaries and additives can be water-binding substances, thickeners, fillers, perfume, dyestuffs, emulsifiers, active compounds, such as vitamins, preservatives, water and/or salts.

During processing of the ubiquinones and other oxidation-sensitive substances, the temperature should not be above 40° C. Otherwise, the usual rules, which are known to the expert, are to be observed.

The substance groups according to the invention can thus be incorporated into all cosmetic bases. In principle, however, W/O and O/W and W/O/W emulsions are preferred. Combinations according to the invention can be employed particularly advantageously in care products, such as, for example, O/W creams, W/O creams, O/W lotions, W/O lotions and the like.

Unless stated otherwise, all the amounts data, percentage data or parts relate to the weight, in particular the total weight of the formulations or of the particular mixture.

The following examples serve to describe the invention without the intention being to limit the invention to these examples.

The parts stated are parts by weight.

EXAMPLE I

Skin cream of the W/O type

|  | Parts by weight |
|---|---|
| Vaseline DAB 9 | 13 |
| Glycerol DAB 9 | 6.3 |
| Water (CDS, completely desalinated) | 34.4 |
| Paraffin oil (Mineral oil 5E, Shell) | 35 |
| Cetearyl alcohol/PEG 40-castor oil/sodium cetearyl sulphate (Emulgade F, Henkel KGaA) | 2.5 |

The aqueous phase, heated at 75° C., is added to the fat phase, heated at 75° C., and the components are stirred and homogenized until a uniformly white cream has formed. 0.3 part of coenzyme Q10 are dissolved in 8.5 parts of paraffin oil, the solution is added to the cream, which has been cooled to about 40° C., and the components are stirred until a uniform pale yellow cream has formed.

Example I has the following final composition:

|  | Parts by weight |
|---|---|
| Vaseline DAB 9 | 13 |
| Glycerol DAB 9 | 6.3 |
| Water (CDS, completely desalinated) | 34.4 |
| Paraffin oil (Mineral oil 5E, Shell) | 43.5 |
| Cetearyl alcohol/PEG 40-castor oil/sodium cetearyl sulphate (Emulgade F, Henkel KGaA) | 2.5 |
| coenzyme Q10 | 0.3 |
|  | 100.0 |

EXAMPLE II

Skin cream of the W/O type

|  | Parts by weight |
|---|---|
| PEG 1-glyceryl oleostearate + paraffin wax | 8 |
| Vaseline DAB | 2.8 |
| Paraffin oil (Mineral oil 5E, Shell) | 9.9 |
| Paraffin wax/paraffin | 1.8 |
| Ceresin | 2.2 |
| Octyldodecanol (Eutanol G) | 10 |
| Propylene glycol | 1 |
| Glycerol | 1 |
| Magnesium sulphate | 0.7 |
| Water CDS | 59.7 |
| Total additives (perfume, preservation, stabilization) | 0.8 |

The aqueous phase, heated at 75° C., is added to the fat phase, heated at 75° C., and the components are stirred and homogenized until a uniformly white cream has formed. 0.36 part of coenzyme Q10 and 0.04 part of coenzyme Q6 are dissolved in 2 parts of paraffin oil, the solution is added to the cream, which has been cooled to about 40° C., and the components are stirred until a uniform pale yellow cream has formed.

Example II has the following final composition:

|  | Parts by weight |
|---|---|
| PEG 1-glyceryl oleostearate + paraffin wax | 8 |
| Vaseline DAB | 2.8 |
| Paraffin wax/paraffin | 1.8 |
| Paraffin oil (Mineral oil 5E, Shell) | 11.9 |
| Ceresin | 2.2 |
| Octyldodecanol | 10 |
| Coenzyme Q6 | 0.04 |
| Coenzyme Q10 | 0.36 |
| Propylene glycol | 1 |
| Glycerol | 1 |
| Magnesium sulphate | 0.7 |
| Water CDS | 59.4 |
| Total additives | 0.8 |
| (perfume, preservation, stabilization) |  |
|  | 100 |

EXAMPLE III

Skin cream of the O/W type

|  | Parts by weight |
|---|---|
| Octyldodecanol (Eutanol G, Henkel KGaA) | 9.3 |
| Cetearyl alcohol/PEG 40-castor oil/sodium cetearyl sulphate (Emulgade F, Henkel KGaA) | 3.7 |
| Water CDS | 73.7 |
| Glycerol DAB 9 | 4.6 |
| Paraffin oil (Mineral oil 5E, Shell) | 5.8 |

The aqueous phase, heated at 75° C., is added to the fat phase, heated at 75° C., and the components are stirred and homogenized until a uniformly white cream has formed. 0.54 part of coenzyme Q10 and 0.36 part of coenzyme Q6 are dissolved in 2 parts of paraffin oil, the solution is added to the cream, which has been cooled to about 40° C., and the components are stirred until a uniform pale yellow cream has formed.

Example III has the following final composition:

|  | Parts by weight |
|---|---|
| Octyldodecanol (Eutanol G, Henkel KGaA) | 9.3 |
| Cetearyl alcohol/PEG 40-castor oil/sodium cetearyl sulphate (Emulgade F, Henkel KGaA) | 3.7 |
| Water CDS | 73.7 |
| Glycerol DAB 9 | 4.6 |
| Paraffin oil (Mineral oil eE, Shell) | 7.8 |
| Coenzyme Q6 | 0.36 |
| Coenzyme Q10 | 0.54 |
|  | 100 |

EXAMPLE IV

O/W lotion

| | Parts by weight |
|---|---|
| Steareth-2 | 3 |
| Steareth-21 | 2 |
| Cetearyl alcohol/PEG 40-castor oil/ sodium cetearyl sulphate (Emulgade F, Henkel KGaA) | 2.5 |
| Paraffin oil (Mineral oil 5E, Shell) | 10.1 |
| Propylene glycol | 1 |
| Glycerol | 1 |
| Water CDS | 74.3 |
| Total additives (perfume, preservation, stabilization) | 0.8 |

The aqueous phase, heated at 75° C., is added to the fat phase, heated at 75° C., and the components are stirred and homogenized until a uniformly white cream has formed. 0.2 part of coenzyme Q10 and 0.2 part of coenzyme Q6 are dissolved in 4 parts of paraffin oil, the solution is added to the lotion, which has been cooled to about 40° C., and the components are stirred until a uniform pale yellow lotion has formed.

Example IV has the following final composition:

| | Parts by weight |
|---|---|
| Steareth-2 | 3 |
| Steareth-21 | 2 |
| Cetearyl alcohol/PEG 40-castor oil/ sodium cetearyl sulphate (Emulgade F, Henkel KGaA) | 2.5 |
| Paraffin oil (Mineral oil 5E, Shell) | 14.1 |
| Propylene glycol | 1 |
| Coenzyme Q6 | 0.2 |
| Coenzyme Q10 | 0.2 |
| Glycerol | 1 |
| Water CDS | 74.3 |
| Total additives (perfume, preservation, stabilization) | 0.8 |
| | 100 |

EXAMPLE V

O/W lotion

| | Parts by weight |
|---|---|
| Octyldodecanol (Eutanol G, Henkel KGaA) | 5.6 |
| Cetearyl alcohol/PEG 40-castor oil/ sodium cetearyl sulphate (Emulgade F, Henkel KGaA) | 8.9 |
| Cetearyl isononanoate (Cetiol 5N, Henkel KGaA) | 7.5 |
| Water CDS | 62.3 |
| Glycerol DAB 9 | 4.7 |
| Paraffin oil (Mineral oil 5E, Shell) | 5.7 |

The aqueous phase, heated at 75° C., is added to the fat phase, heated at 75° C., and the components are stirred and homogenized until a uniformly white cream has formed. 0.04 part of coenzyme Q10 and 0.36 part of coenzyme Q6 are dissolved in 4 parts of paraffin oil, the solution is added to the cream, which has been cooled to about 40° C., and the components are stirred until a uniform pale yellow cream has formed.

Example V has the following final composition:

| | Parts by weight |
|---|---|
| Octyldodecanol (Eutanol G, Henkel KGaA) | 5.6 |
| Cetearyl alcohol/PEG 40-castor oil/ sodium cetearyl sulphate (Emulgade F, Henkel KGaA) | 8.9 |
| Cetearyl isononanoate (Cetiol 5N, Henkel KGaA) | 7.5 |
| Water CDS | 62.3 |
| Glycerol DAB 9 | 4.7 |
| Paraffin oil (Mineral oil 5E, Shell) | 10.7 |
| Coenzyme Q6 | 0.04 |
| Coenzyme Q10 | 0.36 |
| | 100 |

EXAMPLE VI

Skin oil

| | Parts by weight |
|---|---|
| Glyceryl tricaprylate (Miglyol 812, Dynamit Nobel) | 21 |
| Hexyl laurate (Cetiol A, Henkel KGaA) | 20 |
| Octyl stearate (Cetiol 886, Henkel KGaA) | 20 |
| Paraffin oil (Mineral oil 5E, Shell) | 35 |
| Coenzyme Q6 | 2 |
| | 100 |

The components are stirred at 25° C. until a uniform clear mixture has formed.

EXAMPLE VII

Skin oil

| | Parts by weight |
|---|---|
| Glyceryl tricaprylate (Miglyol 812, Dynamit Nobel) | 21 |
| Hexyl laurate (Cetiol A, Henkel KGaA) | 20 |
| Octyl stearate (Cetiol 886, Henkel KGaA) | 20 |
| Paraffin oil (Mineral oil 5E, Shell) | 35 |
| Coenzyme Q6 | 2 |
| | 100 |

The preparation is carried out as described in Example VI.

We claim:

1. A method for treating senile xerosis and exogenous aging of the skin which comprises applying to said skin an effective amount of a formulation consisting essentially of 1. one or more ubiquinones or their derivatives or both, and 2. as a pharmaceutical or cosmetic base, one or more members selected from the group consisting of oil components, fats, waxes, emulsifiers, anionic, cationic, ampholytic, zwifter-ionic surfactants, nonionic surfactants, lower mono- and polyhydric alcohols, water, preservatives, buffer substances, thickeners, fragrances, dyestuffs, and opacifying agents, and 3. optionally, one or more members selected from the group consisting of vitamin E, vitamin C, imidazoles, alpha-hydroxycarboxylic acids, iron complexing agents and UV light protection filters, U.V. absorbers and 4. optionally, one or more members selected from the group consisting of creatine, guanine, guanosine, adenine, adenosine, nicotine, nicotinamide, and riboflavin, and 5. optionally, one or more members selected from the group consisting of pantothenic acid, panthenol, liponic acid and niacin, and 6. optionally, one or more members selected from the group consisting of L-carnitine and uridine, and 7. optionally, one or more members selected from the group consisting of hexoses, pentoses and fatty acids, and 8. optionally, one or more members selected from the group consisting of citric acid, pyruvate and glutathione, and 9. optionally, antioxidants, and 10. optionally, thickeners, and 11. optionally, fillers, and 12. optionally, dyestuffs, and 13. optionally, preservatives.

2. The method according to claim 1, wherein the ubiquinone has 0 to 12 isoprene units and/or alkyl radicals.

3. The method according to claim 1, wherein the formulation contains an antioxidant or a U.V. absorber.

4. The method according to claim 1, wherein the formulation is a cosmetic or dermatological formulation.

5. The method according to claim 1, wherein the formulation is a W/O emulsion, a O/W emulsion or a W/O/W emulsion.

* * * * *

UNITED STATES PATENT AND TRADEMARK OFFICE
CERTIFICATE OF CORRECTION

PATENT NO : 5,912,272
DATED : June 15, 1999
INVENTOR(S): Udo HOPPE, et al.

It is certified that error appears in the above-identified patent and that said Letters Patent is hereby corrected as shown below:

Column 9, line 4,  cancel "zwifter-ionic" and substitute --zwitter-ionic--

Signed and Sealed this

Seventh Day of December, 1999

Attest:

Q. TODD DICKINSON

Attesting Officer

Acting Commissioner of Patents and Trademarks